(12) United States Patent
Miller et al.

(10) Patent No.: US 6,582,229 B1
(45) Date of Patent: Jun. 24, 2003

(54) METHODS FOR MODELING BITE REGISTRATION

(75) Inventors: Ross J. Miller, Sunnyvale, CA (US); Eric Kuo, Foster City, CA (US); Daniel E. Falvey, Castro Valley, CA (US); Andrew H. Trosien, San Francisco, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 09/843,244

(22) Filed: Apr. 25, 2001

Related U.S. Application Data

(60) Provisional application No. 60/199,485, filed on Apr. 25, 2000.

(51) Int. Cl.$^7$ .............................................. A61C 11/00
(52) U.S. Cl. ......................................... 433/213; 433/71
(58) Field of Search ........................... 433/215, 68, 69, 433/213, 71

(56) References Cited

U.S. PATENT DOCUMENTS

| | | | |
|---|---|---|---|
| 5,340,309 A | * | 8/1994 | Robertson .................... 433/69 |
| 5,605,459 A | * | 2/1997 | Kuroda et al. .............. 433/213 |
| 5,879,158 A | | 3/1999 | Doyle et al. |
| 5,905,658 A | | 5/1999 | Baba |
| 6,089,868 A | | 7/2000 | Jordan et al. |
| 6,152,731 A | | 11/2000 | Jordan et al. |

* cited by examiner

*Primary Examiner*—Todd E Manahan
(74) *Attorney, Agent, or Firm*—Townsend and Townsend and Crew LLP

(57) ABSTRACT

The present invention provides methods and devices for determining an axis of upper and lower jaw articulation of a patient and modeling jaw movement about such an axis, particularly with the use of computerized visual images. The methods comprise providing digital data sets of tooth and bite configuration information which may be used to determine an estimated condylar axis of rotation for a patient. A number of data sets may be acquired and utilized for such estimations. Data sets may be obtained with the use of bite registers. Such registers may be formed by a number of methods and device designs of the present invention. The resulting digital data sets and axis of articulation may then be utilized to generate animated visual images of a patient's jaws in various bite configurations throughout a given rotation around the determined axis. Accuracy of such dynamic imaging, in addition to the determination of the location of the condylar axis, may increase with the number of bite configurations recorded throughout the rotation.

21 Claims, 5 Drawing Sheets

METHODS FOR MODELING BITE REGISTRATION

CROSS-REFERENCES TO RELATED APPLICATIONS

The present application claims benefit of provisional Application No. 60/199,485, filed on Apr. 25, 2000, the full disclosure of which is incorporated herein by reference.

SUMMARY OF THE INVENTION

The present invention provides methods and devices for determining an axis of upper and lower jaw articulation of a patient and modeling jaw movement about such an axis, particularly with the use of computerized visual images. The methods comprise providing digital data sets of tooth and bite configuration information which may be used to determine an estimated condylar axis of rotation for a patient. A number of data sets may be acquired and utilized for such estimations. In a preferred embodiment, data sets representing the upper jaw, lower jaw and at least two bite registers may be used to determine an axis of rotation. In an additional embodiment, data sets representing at least a first and a second bite configuration may be used to determine such an axis of rotation. Such bite configurations may be guided with the use of bite registers. The above mentioned bite registers may be formed by a number of methods and device designs of the present invention. The resulting digital data sets and axis of articulation may then be utilized to generate animated visual images of a patient's jaws in various bite configurations throughout a given rotation around the determined axis. Accuracy of such dynamic imaging, in addition to the determination of the location of the condylar axis, may increase with the number of bite configurations recorded throughout the rotation.

In a first aspect of the methods of the present invention, digital data sets representing the upper jaw of a patient, the lower jaw of the patient and at least two bite registers may be used to determine an axis of rotation or articulation for the patient's jaws. Digital data sets representing an object may be provided by scanning the object or a three-dimensional model of the object. The jaws of the patient may be modeled by producing a plaster cast of the patient's teeth. After the tooth cast is obtained, it may be digitally scanned using a conventional laser scanner or other range acquisition system to produce the digital data set. A bite register may be similarly scanned to obtain a bite digital data set representing the register.

In a second aspect of the methods of the present invention, a bite register may be formed by a number of methods using a variety of bite registration devices. Bite registers may record the shape, location and orientation of the teeth of the upper jaw in relation to the teeth of the lower jaw when the jaws are in a given bite configuration. In general, it is only necessary to record the features and orientations of an adequate number of teeth to determine the orientations of the remaining teeth. Thus, bite registers are typically structures having an impression of at least a surface of a tooth in the upper jaw and a surface of a tooth in the lower jaw when the upper and lower jaws are in a predetermined bite position.

In a first embodiment, a bite register may be produced by biting a structure comprised of malleable material between the occlusional surfaces of the posterior teeth. In this case, the structure may be a block of such material having a predetermined thickness. When placed on both sides of the mouth between the posterior teeth, as described, the patient may then bite down on the blocks to record the bite configuration. Since the blocks are comprised of a malleable material, such as wax, polyvinyl silaxane, acrylic, plastic, plaster or any other suitable impression material, the teeth and associated dental features, such as gingiva, will imprint in the blocks. It may be appreciated that one continuous block may be used rather than two separate blocks, one on each side of the mouth, or any other shape and/or number of such blocks to effectively form an impression of the occlusional surfaces.

The above described methodology of forming a bite register records a bite configuration at one point in rotation of the jaws around the condylar axis. Starting from a closed position, the lower jaw rotates around the condylar axis as the bite opens to a fully opened position. A bite configuration may be registered or recorded at any point in this rotation. The point in rotation may be preselected by the thickness of the block prior to impression in the above described example. The thicker the block, the more open the bite. Thus, a series of bite registers may be formed with blocks of increasing thickness to model the bite configurations throughout the rotation or throughout a specific range of the rotation. Such a series may be comprised of two, three, four, five, or more of such bite registers, each of which may be scanned to provide a series of bite digital data sets.

In a second embodiment, a bite register may be produced by pressing a structure comprised of malleable material against the facial surfaces of the anterior teeth. It has been determined that the orientations or spatial relationships of the anterior teeth of the upper and lower jaws may adequately determine the orientations of the remaining teeth in a given bite configuration. Such a structure may be comprised of the malleable material itself, or it may be supported by a holder. The holder may be comprised of a plate, contoured to generally fit a dental arch curve, and a handle. The plate may support a malleable material, such as that described previously, and may be pressed against the facial surfaces of the anterior teeth.

Alternatively, in a third embodiment, the holder may be comprised of an upper portion and a lower portion joined by a separator to orient the upper and lower jaws in a predetermined bite position. Malleable material may be mounted on the upper and lower portions of the holder to form registration surfaces. An upper registration surface may contact a surface of a tooth in an upper jaw of a patient and a lower registration surface may contact a surface of a tooth in a lower jaw of a patient. Simultaneous contact of these registration surfaces against the appropriate teeth, by, for example, biting the registration device, may record bite information correlated to the predetermined orientation of the registration surfaces. Such orientation may be fixed or it may be adjustable to join the upper and lower registration surfaces in a series of predetermined orientations. In either case, the bite information may comprise the shape, location and orientation of at least one tooth surface in the upper jaw of a patient in relation to at least one tooth surface in the lower jaw of the patient.

Again, the above described methodology of forming a bite register records a bite configuration at one point in rotation of the jaws around the condylar axis. A bite configuration may be registered or recorded at any point in this rotation. The point in rotation may be preselected by opening the jaws to a desired configuration by any means. In the case of bite registration devices comprising a separator, the registration surfaces may be separated and oriented to open the jaws to a desired configuration based on the characteristics of the separator. The separator may join the upper and lower registration surfaces in a fixed predetermined orientation, or the separator may be adjustable to join the registration surfaces in a series of orientations. In any case, a series of bite registers may be formed to model the bite configurations throughout the rotation or throughout a specific range of the rotation. Such a series may be comprised of two, three, four, five, or more of such bite registers, each of which may be scanned to provide a series of bite digital data sets.

In a third aspect of the methods of the present invention, determination of an axis of upper and lower jaw articulation of a patient and modeling of jaw movement about such an axis may be achieved, particularly with the use of computerized visual images.

In a fourth aspect of the methods of the present invention, digital data sets representing a first bite configuration and a second bite configuration may be used to determine an axis of rotation or articulation for the patient's jaws. This is similar to the first aspect of the methods of the present invention, described above, but utilizes different data sets to determine an axis of rotation. Rather than scanning the upper jaw, lower jaw and bite registrations separately to obtain individual representative digital data sets, the components may be assembled in a bite configuration and scanned together. For example, a plaster cast of the lower jaw may be positioned with the teeth facing upwards. A bite register may then be placed on the cast of the lower jaw, and a plaster cast of the upper jaw may be placed over the cast of the lower jaw with the teeth downwards, guided by and resting on the bite register. In this manner, the plaster casts of a patient's upper and lower dentition to be placed relative to one another in a given bite configuration. A cylindrical scan may then acquired for the lower and upper casts in their relative positions. The scanned data provides a digital model representing an object which is the combination of the patient's arches positioned in a first bite configuration. This may be repeated for a second bite configuration. The second bite configuration may be any desired bite configuration which is different from the first bite configuration. To accomplish this, a new bite register may be obtained from the patient in the second bite configuration. Casts of the teeth may be assembled and scanned as described above.

Once digital data sets are acquired, by any method, an image can be presented and manipulated on a suitable computer system equipped with computer-aided design software. The image manipulation may comprise rotating an image of the lower jaw around the determined axis of articulation to model the movement of a patient's jaws. Such movement may range between a closed position and a fully open position or a portion of the range therein. The computer system may be provided with rules and algorithms which move the jaw(s) in a fully automatic manner, i.e. without user intervention. Such rules and algorithms may be based on the digital data sets representing the differing bite configuration and the determined axis of articulation.

Although a few known bite configurations may be represented, it may be desired to interpolate intermediate bite configurations between the known configurations to visually portray a range of jaw movement. Usually, the successive digital data sets representing these intermediate bite configurations are produced by determining positional differences between selected individual teeth in a digital data set of a first bite configuration and digital data set of a second bite configuration and interpolating said differences. Such interpolation may be performed over as many discrete stages as may be desired, usually at least three, often at least four, more often at least ten, sometimes at least twenty-five, and occasionally forty or more. Many times, the interpolation will be linear interpolation for some or all of the positional differences. Alternatively, the interpolation may be non-linear.

Often, the user will specify certain target intermediate bite configurations, referred to as "key frames," which are incorporated directly into the intermediate digital data sets. The methods of the present invention then determine successive digital data sets between the key frames in the manner described above, e.g. by linear or non-linear interpolation between the key frames. The key frames may be determined by a user, e.g. the individual manipulating a visual image at the computer used for generating the digital data sets.

DESCRIPTION OF THE SPECIFIC EMBODIMENTS

Bite configurations may be recorded with the use of a bite register. A bite register is a device which records the shape, location, and orientation of the teeth of the upper jaw in relation to the teeth of the lower jaw when the jaws are in a given bite configuration. These relationships may then be used to recreate the bite configuration with mechanical models or computerized images of the teeth. If a series of bite configurations are recorded, for example from a closed bite configuration to a fully open bite configuration, the full rotation of the condylar axis may be modeled for a given patient. Accuracy of the dynamic modeling, in addition to the determination of the location of the condylar axis, may increase with the number of bite configurations recorded throughout the rotation.

Figure 1A:
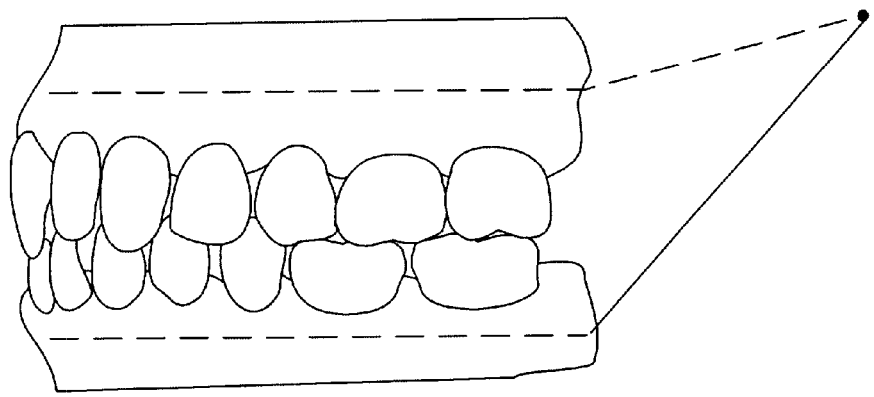
FIGS. 1A–1C show various bite configurations of a patient illustrating the orientations of the upper and lower jaws in rotation about the condylar axis.
Figure 1B:
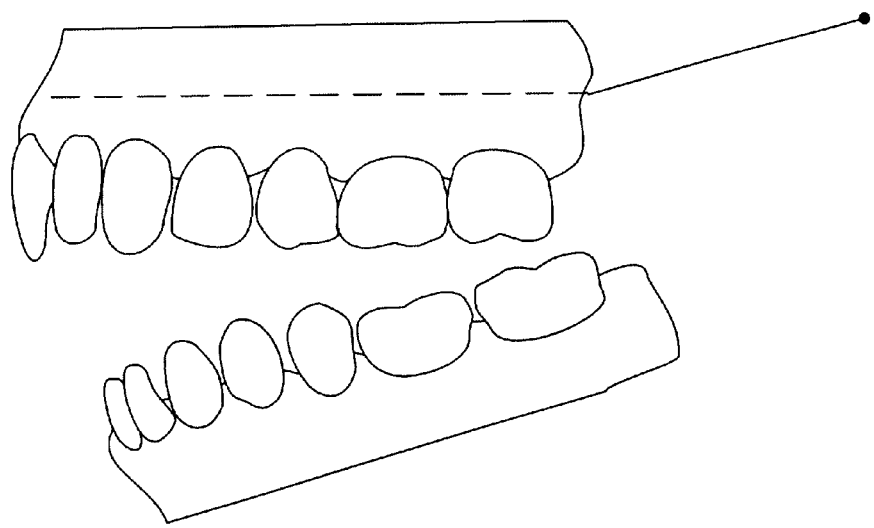
Figure 1C:
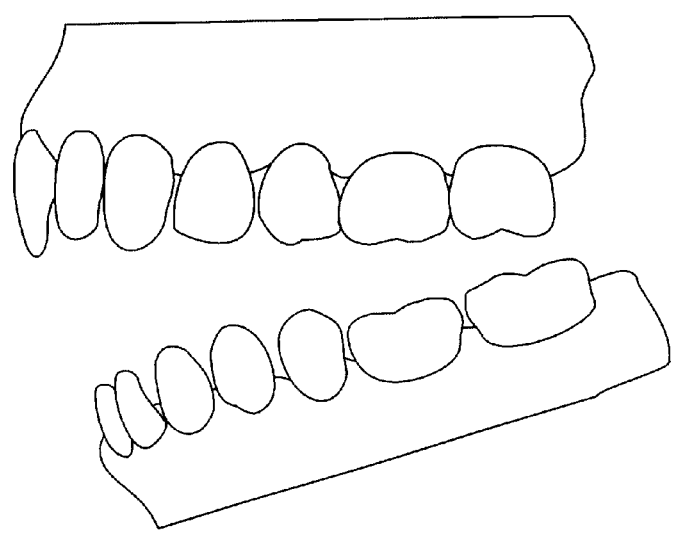
Figure 2:
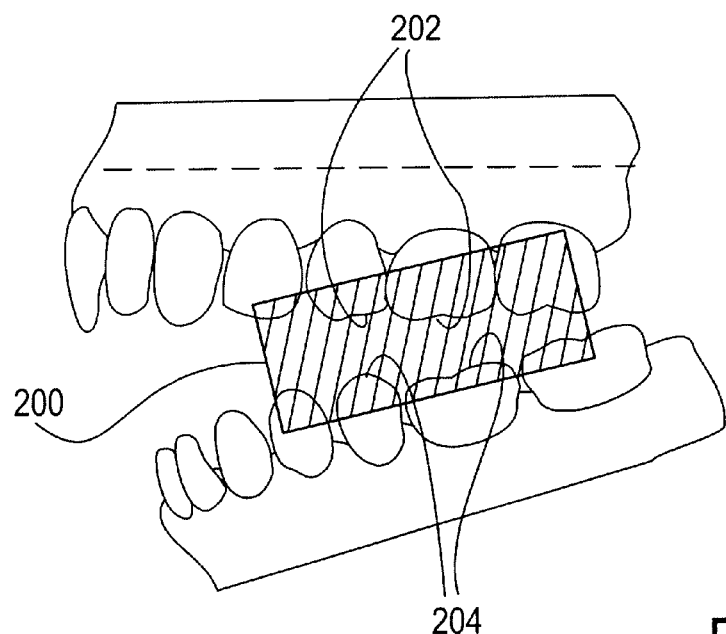
FIG. 2 is a side view of a the upper and lower jaws of a patient registering a bite in a block of malleable material placed between the occlusional surfaces of the posterior teeth.
Figure 3:
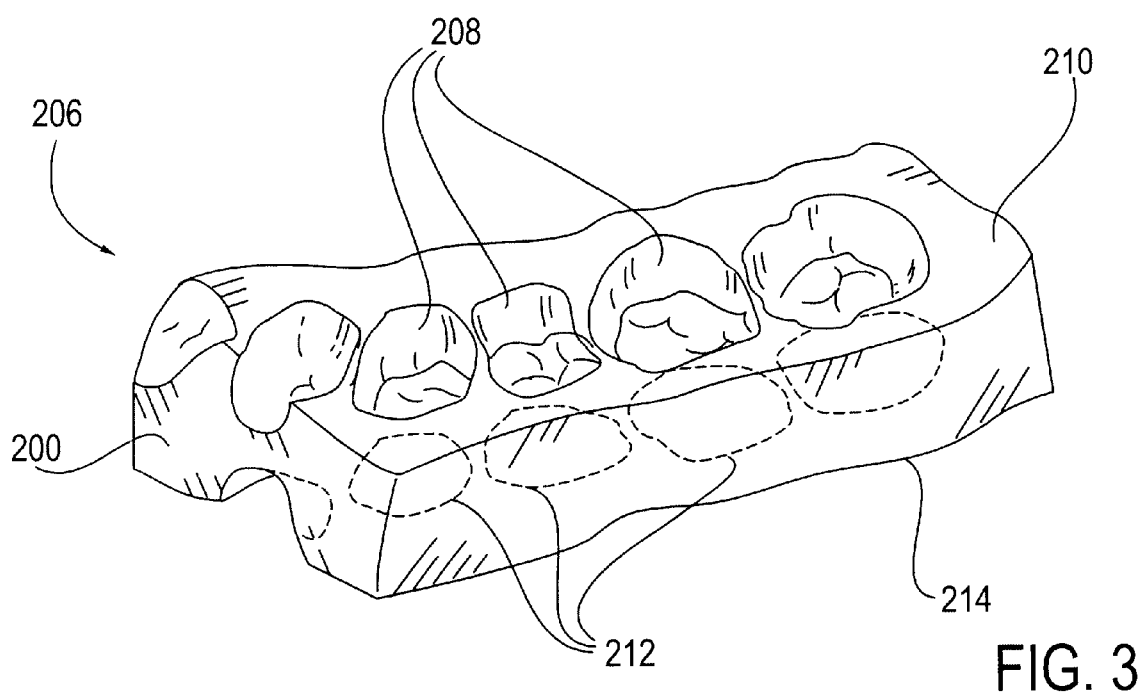
FIG. 3 is a perspective view of a bite register resulting from the formation illustrated in FIG. 2.

A number of methodologies may be used to record bite configurations to form a bite register. In general, bite registers record the features and orientations of an adequate number of teeth to determine the orientations of the remaining teeth. This is typically achieved by forming impressions of the teeth of both the upper and lower jaws when the jaws are in a biting configuration. Referring to FIG. 2, this may be achieved by placing a block 200 of malleable material between the occlusional surfaces of the upper and lower posterior teeth 202, 204 of a patient as shown. Typically, two such blocks 200 may be used, one placed on the right side of the mouth and one in the same or similar position on the left side. Thus, when the patient bites down on the blocks 200, the bite configuration on both sides of the mouth may be recorded simultaneously. Since the block 200 is comprised of a malleable material, such as wax, polyvinyl silaxane, acrylic, plastic, plaster or any suitable impression material, the teeth 202, 204 will imprint or form depressions in the block 200 corresponding to the shapes, locations and orientations of the teeth 202, 204. The result, as shown in FIG. 3, is a bite register 206. Here, impressions 208 of the surfaces of the teeth and associated dental features, such as gingiva, in the top jaw may be seen in the top surface 210 of the block 200. Similarly, impressions 212 of the surfaces of the teeth and associated dental features in the bottom jaw may be made in the bottom surface 214 of the block 200, represented by dashed lines. Thus, spatial relationships between the upper jaw and the lower jaw may be recorded.

The above described methodology of forming a bite register records a bite configuration at one point in rotation of the jaws around the condylar axis. Starting from a closed position, the lower jaw rotates around the condylar axis as the bite opens to a fully opened position. A bite configuration may be registered or recorded at any point in this rotation. The point in rotation may be preselected by the thickness of the block prior to impression in the above described example. The thicker the block, the more open the bite. Thus, a series of bite registers may be formed with blocks of increasing thickness to model the bite configurations throughout the rotation or throughout a specific range of the rotation.

In a preferred embodiment of a method of the present invention, a bite register may be comprised of an impression of the facial surfaces of the anterior teeth. It has been determined that the orientations or spatial relationships of the anterior teeth of the upper and lower jaws may adequately determine the orientations of the remaining teeth in a given bite configuration. In particular, the spatial relationships between the facial surfaces of the incisors may be adequate to model a bite configuration. Using these surfaces to form a bite register provide a number of advantages: 1) the facial surfaces of the anterior teeth are easily accessible for impression formation since the surfaces lie against the lips, 2) the surfaces required for adequate modeling of the bite configuration may be relatively low, typically requiring only the anterior surfaces of the incisors, possibly only requiring one surface on the top jaw and a correlating surface on the bottom jaw, and 3) variability in the point in the condylar axis rotation chosen for a given bite configuration may be reduced since the jaws may be opened to a given point in the rotation by non-malleable supports. In the previously described method, the jaws were set to a given point in the rotation by the thickness of a block of malleable material placed between the jaws. However, the act of biting the blocks may compress the blocks to an undetermined thickness, increasing the variation in actual axis rotation. In the above described embodiment of a method of the present invention, the jaws may be set to a given point in the rotation by any means, such as shim stock or non-malleable supports placed between the jaws. The bite may then be registered by forming an impression of the facial surfaces of the anterior teeth as described.

Figure 4:
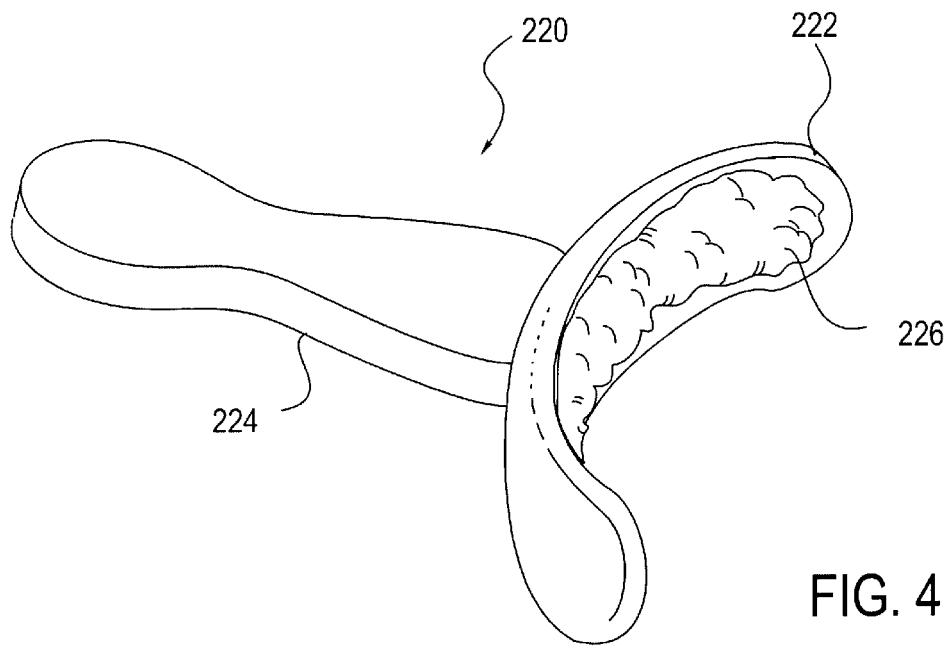
FIG. 4 is a illustration of a bite registration device.
Figure 5:
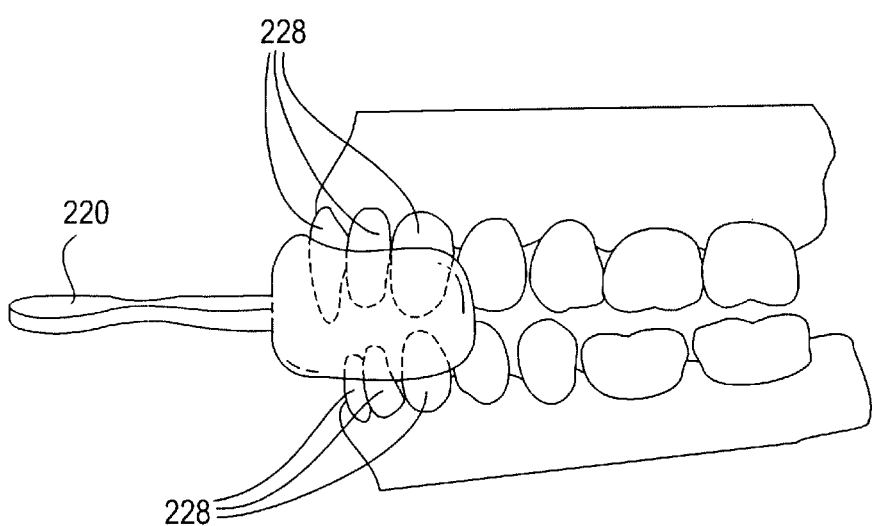
FIG. 5 illustrates a bite registration device, as shown in FIG. 4, in use to form a bite register.
Figure 6:
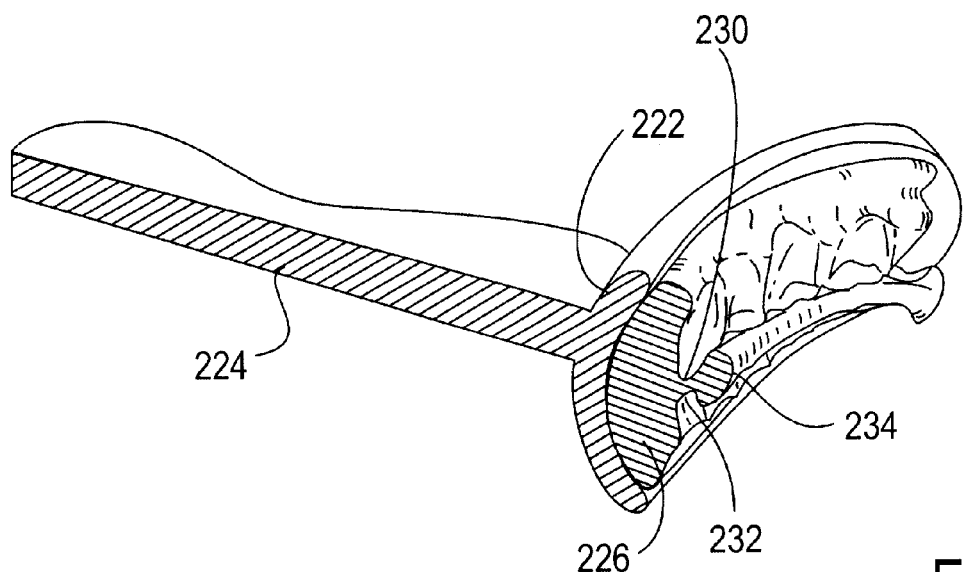
FIG. 6 illustrates a bite register formed by a method as shown in FIG. 5.

Referring to FIG. 4, such an impression may be made with the use of a holder 220. Such a holder 220 may be comprised of a plate 222, contoured to generally fit a dental arch curve, and a handle 224. The plate 222 may support a malleable material 226, such as wax, polyvinyl silaxane, acrylic, plastic, plaster or any suitable impression material, into which an impression may be made. As shown in FIG. 5, the material (not shown) and holder 220 may be pressed against the facial surfaces of the anterior teeth 228. In this manner, the material 226 may contact the facial tooth surfaces and press through any space between the teeth of the upper and lower jaws. Thus, the material may also contact some occlusional and lingual surfaces of the teeth 228. This is particularly the case when the bite is at least partially open. The resulting bite registration may appear as in FIG. 6. Here, a cross-section of the material 226, plate 222 and handle 224 are shown to illustrate typical contours of the impression in the malleable material 226. An upper depression 230 may reflect the surfaces of an incisor in the upper jaw and a lower depression 232 may reflect the surfaces of an incisor in the lower jaw. A protrusion 234 may be formed between these depressions 230, 232 due to the material 226 pressing between the jaws. Similar impressions or depressions from the surfaces of the surrounding teeth may be seen in perspective view in FIG. 6.

It may be appreciated that the curvature of the plate may serve to provide improved contact of the malleable material with the facial tooth surfaces. However, the plate may have any contour to achieve desired results. Also, the malleable material may be used without the holder or similar device. In such a case, the material itself may simply be pressed against the teeth.

Figure 7:
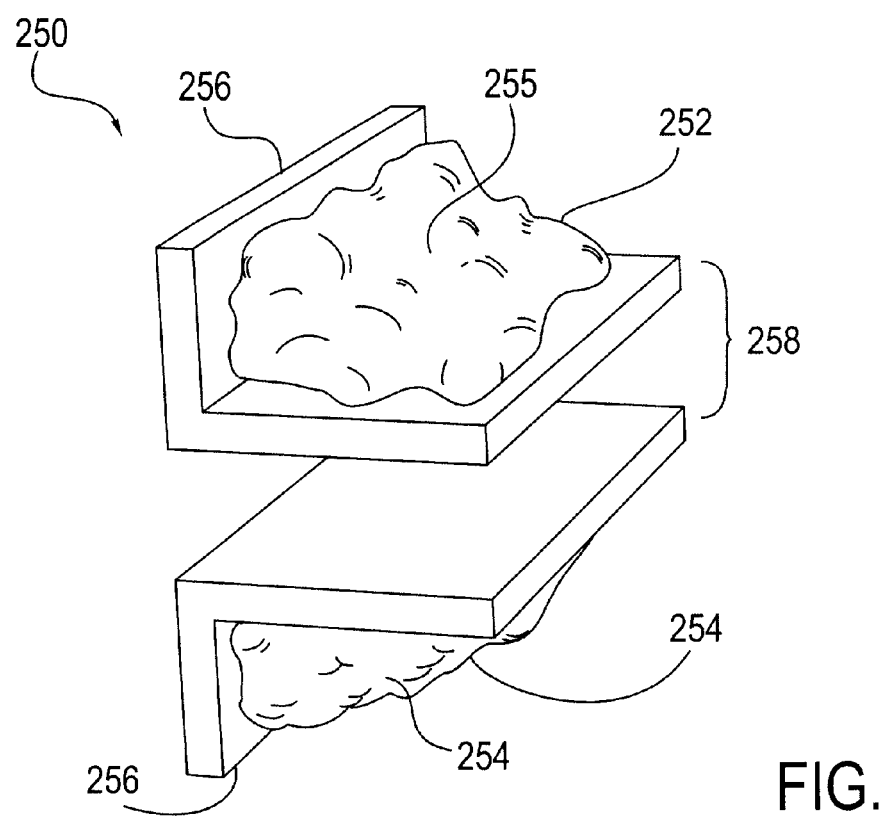
FIG. 7 is a perspective view of a bite registration device having an adjustable separation between bite registration surfaces.
Figure 8:
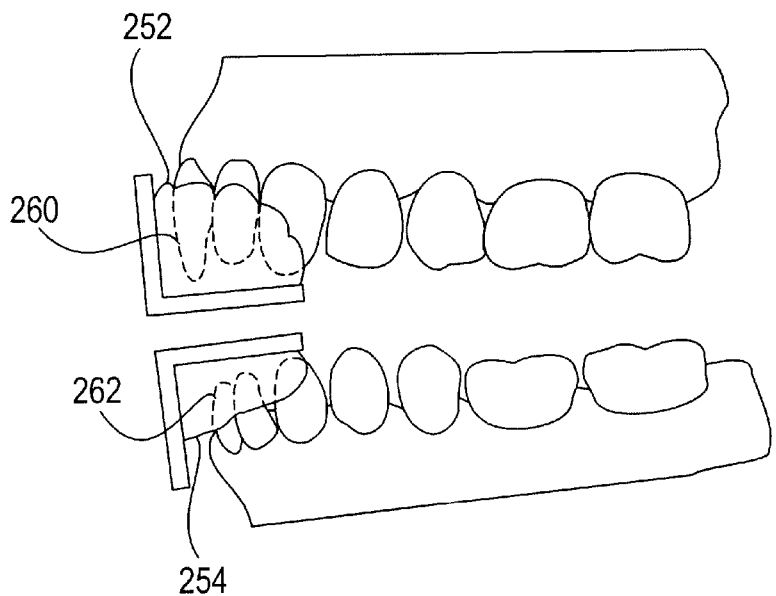
FIG. 8 illustrates a bite registration device, as shown in FIG. 7, in use to form a bite register.

Referring to FIG. 7, a preferred embodiment of a bite registration device 250 to form an impression of the facial surfaces of the anterior teeth is depicted. Such a device 250 may be comprised of an upper registration surface 252, a lower registration surface 254 and a separator 255 joining the upper and lower registration surfaces 252, 254. In this example, each registration surface is comprised of malleable material 255 supported by a holder 256. The holders 256 are attached to the separator 255 which holds the registration surfaces 252, 254 apart at a desired distance 258. In this example, the separator 255 is adjustable so that the distance 258 between the registration surfaces 252, 254 may be set to a desired amount of separation. It may also be possible for the separator 255 to adjust the orientation of the registration surfaces 252, 254, such as varying the tilt of the surfaces and/or the spatial relationship between the two surfaces. To form a bite register, as illustrated in FIG. 8, a patient may bite the bite registration device 250 so that a surface of a tooth in the upper jaw 260 contacts the upper registration surface 252 and a surface of a tooth in the lower jaw 262 contacts the lower registration surface 254. Such contact forms an impression of the tooth surfaces 260, 262 in the registration surfaces 252, 254, thus recording the bite configuration. When biting the registration device 250, the predetermined orientations of the registration surfaces 252, 254 may set the jaws to a given point in rotation about the condylar axis. Thus, the further apart the registration surfaces 252, 254 are set, the more open the bite configuration becomes. This may ensure the recording of a bite configuration at a specific point in rotation about the condylar axis, and it may reduce variability in such recording. To record bite configurations throughout a portion of the range of rotation, a number of bite registers may be made with the registration surfaces at differing separation distances.

Figure 9:
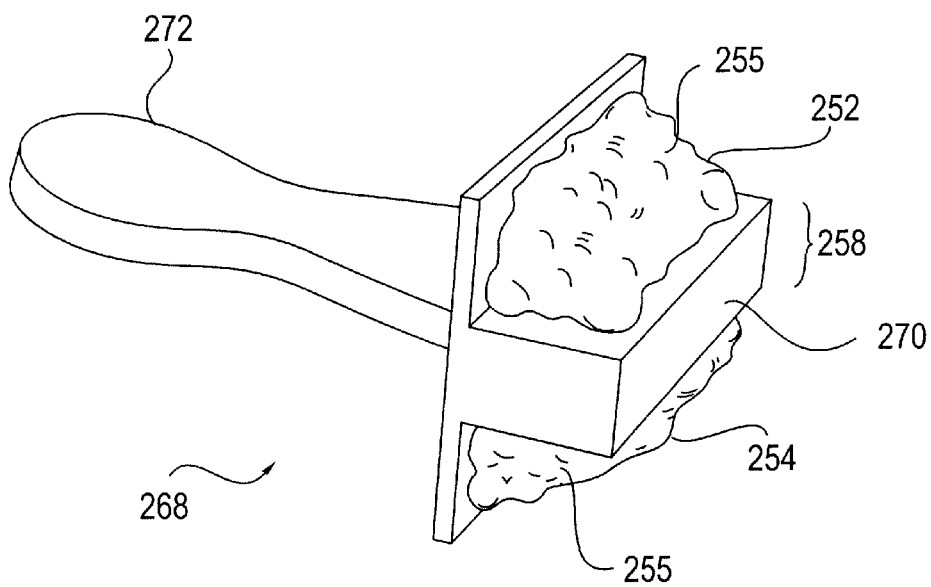
FIG. 9 is a perspective view of a bite registration device having a fixed separation between bite registration surfaces.

This may easily be achieved with an adjustable registration device, as described above. However, this may also be achieved with the use of a number of registration devices, each with a fixed separation distance. Such a device embodiment is depicted in FIG. 9. Here, the registration surfaces 252, 254 are comprised of a malleable material 255 supported by a separator 270, which is attached to a handle 272. The separator 270 may be a solid structure which holds the material 255 apart at a desired distance 258. The structure may also provide a desired orientation of the registration surfaces 252, 254, providing a specific tilt of the surfaces and/or a spatial relationship between the two surfaces. To form a bite register, a patient may bite the bite registration device 268 so that a surface of a tooth in the upper jaw 260 contacts the upper registration surface 252 and a surface of a tooth in the lower jaw 262 contacts the lower registration surface 254, as previously depicted in FIG. 8. Again, such contact forms an impression of the tooth surfaces 260, 262 in the registration surfaces 252, 254, thus recording the bite configuration. When biting the registration device 268, the predetermined orientations of the registration surfaces 252, 254 may set the jaws to a given point in rotation about the condylar axis. To record bite configurations throughout a portion of the range of rotation, a number of bite registers may be made with the registration surfaces at differing separation distances.

Bite registers obtained from any method may be used to recreate the bite configuration of a patient with mechanical models or computerized images of the teeth. As previously mentioned, a series of bite registers may be used to model the bite configurations throughout a range of rotation about the condylar axis. A series of such models may then be used to determine the location of the condylar axis.

The present invention provides a method for determining an axis of upper and lower jaw articulation. A preferred embodiment of a method of the present invention utilizes an upper digital data set, representing the upper jaw of the patient, a lower digital data set, representing the lower jaw of the patient, and at least two bite digital data sets, each representing a bite register. However, three or more digital data sets may also be used.

Digital data sets of information to model an object, such as a patient's upper jaw, a patient's lower jaw or a bite register, may be obtained in a variety of ways. For example, the object may be scanned or imaged using well known technology, such as X-rays, three-dimensional X-rays, computer-aided tomographic images or data sets, magnetic resonance images, etc. Methods for digitizing such conventional images to produce data sets useful in the present invention are well known and described in the patent and medical literature. However, digital data sets of a patient's teeth will typically rely on first obtaining a plaster cast of the patient's teeth by well known techniques, such as those described in Graber, Orthodontics: Principle and Practice, Second Edition, Saunders, Philadelphia, 1969, pp. 401–415. After the tooth casting is obtained, it can be digitally scanned using a conventional laser scanner or other range acquisition system to produce the digital data set. The data set produced by the range acquisition system may, of course, be converted to other formats to be compatible with other software. General techniques for producing plaster casts of teeth and generating digital models using laser scanning techniques are described, for example, in U.S. Pat. No. 5,605,459, the full disclosure of which is incorporated herein by reference.

There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

A preferred range acquisition system is an optical, reflective, non-contact-type scanner. Non-contact-type scanners are preferred because they are inherently nondestructive (i.e., do not damage the sample object), are generally characterized by a higher capture resolution and scan a sample in a relatively short period of time. One such scanner is the Cyberware Model 15 manufactured by Cyberware, Inc., Monterey, Calif.

The methods of the present invention will rely on manipulating the data sets at a computer or workstation having a suitable graphical user interface (GUI) and software appropriate for viewing and modifying the generated images. Specific aspects of the software will be described in detail hereinafter.

According to the methods of the present invention, the axis of upper and lower jaw articulation may also be determined by manipulating data sets of bite configurations. A preferred embodiment of such a method will be described. To begin, a bite register is obtained from a patient in a first bite configuration. This may be any desired bite configuration ranging from closed to fully open. The bite register enables mechanical tooth/jaw models, such as plaster casts, to be positioned in a representative bite configuration for scanning. This is usually accomplished by first placing the lower cast in front of the scanner, with the teeth facing upwards, then placing the bite register on top of the lower cast, and finally by placing the upper cast on top of the lower cast, with the teeth downwards, resting on the bite register. A cylindrical scan is then acquired for the lower and upper casts in their relative positions. The scanned data provides a digital model of medium resolution representing an object which is the combination of the patient's arches positioned in the first bite configuration. This may be repeated for a second bite configuration. The second bite configuration may be any desired bite configuration which is different from the first bite configuration. To accomplish this, a new bite register may be obtained from the patient in the second bite configuration. Casts of the teeth may be assembled and scanned as described above.

What is claimed is:

1. A method for determining an axis of upper and lower jaw articulation of a patient, said method comprising:

providing art upper digital data set representing the upper jaw of the patient;

providing a lower digital data set representing the lower jaw of the patient;

providing at least two bite digital data sets, each bite digital data set representing a bite register which records the orientation of at least a portion of the upper and lower jaws in a different bite configuration; and determining an axis of articulation from the upper, lower and bite digital data sets.

2. A method as in claim 1, wherein the step of providing an upper digital data set comprises scanning a three-dimensional model of the patient's upper teeth.

3. A method as in claim 1, wherein the step of providing a lower digital data set comprises scanning a three-dimensional model of the patient's lower teeth.

4. A method as in claim 1, wherein the step of providing a bite digital data set comprises scanning a three-dimensional bite register.

5. A method as in claim 4, wherein the bite register is a structure having an impression of a surface of a tooth in the upper jaw and a surface of a tooth in the lower jaw when the upper and lower jaws are in a predetermined bite position.

6. A method as in claim 5, wherein the structure is comprised of a malleable material into which the impression is made.

7. A method as in claim 6, wherein the material comprises wax, polyvinyl silaxane, acrylic, plastic, plaster or an impression material.

8. A method as in claim 5, wherein the surfaces are occlusional surfaces.

9. A method as in claim 8, wherein the structure is a block of malleable material having a predetermined thickness which is positioned between the occlusional surfaces of the upper and lower teeth when forming the impression.

10. A method as in claim 5, wherein the surfaces are facial surfaces of anterior teeth.

11. A method as in claim 10, wherein the structure is a malleable material which is pressed against the facial surfaces of the anterior teeth.

12. A method as in claim 11, wherein the material is supported by a holder.

13. A method as in claim 12, wherein the holder comprises an upper portion and a lower portion joined by an adjustable separator to orient the upper and lower jaws in a predetermined bite position.

14. A method as in claim 1, further comprising at least three bite digital data sets.

15. A method as in claim 1, further comprising at least five bite digital data sets.

16. A method as in claim 1, further comprising:

presenting a visual image based on the upper digital data set;

presenting a visual image based on the lower digital data set; and manipulating the visual images around the axis of articulation.

17. A method for determining an axis of upper and lower jaw articulation of a patient, said method comprising:

providing a first digital data set representing the upper and lower jaws in a first bite configuration;

providing a second digital data set representing the upper and lower jaws in a second bite configuration; and determining an axis of articulation from the first and second bite configurations.

18. A method as in claim 17, wherein the step of providing a first digital data set comprises scanning a three-dimensional model of a patient's upper and lower teeth in a first desired bite configuration.

19. A method as in claim 17, wherein the step of providing a second digital data set comprises scanning a three-dimensional model of a patient's upper and lower teeth in a second desired bite configuration.

20. A method as in claim 17, wherein the desired bite configurations are guided with the use of a bite register.

21. A method as in claim 17, further comprising a third digital data set representing a third bite configuration and determining an axis of articulation with the use of the first, second and third bite configurations.

* * * * *

UNITED STATES PATENT AND TRADEMARK OFFICE
CERTIFICATE OF CORRECTION

PATENT NO. : 6,582,229 B1
DATED : June 24, 2003
INVENTOR(S) : Miller et al.

It is certified that error appears in the above-identified patent and that said Letters Patent is hereby corrected as shown below:

<u>Column 8,</u>
Line 49, should read -- ...providing an upper digital data set representing the upper... --

Signed and Sealed this

Twenty-first Day of June, 2005

JON W. DUDAS
*Director of the United States Patent and Trademark Office*